(12) United States Patent
Medintz et al.

(10) Patent No.: US 11,795,483 B2
(45) Date of Patent: *Oct. 24, 2023

(54) SELF-ASSEMBLED NANOPLATELET-ENZYME BIOCONJUGATES PROVIDING FOR INCREASED BIOCATALYTIC EFFICIENCY

(71) Applicant: The Government of the United States of America, as represented by the Secretary of the Navy, Arlington, VA (US)

(72) Inventors: Igor L. Medintz, Springfield, VA (US); Joyce Breger, Greenbelt, MD (US); Scott Walper, Springfield, VA (US); Michael H. Stewart, Springfield, VA (US)

(73) Assignee: The Government of the United States of America, as represented by the Secretary of the Navy, Arlington, VA (US)

( * ) Notice: Subject to any disclaimer, the term of this patent is extended or adjusted under 35 U.S.C. 154(b) by 586 days.

This patent is subject to a terminal disclaimer.

(21) Appl. No.: 16/438,081

(22) Filed: Jun. 11, 2019

(65) Prior Publication Data
US 2019/0330666 A1 Oct. 31, 2019

Related U.S. Application Data

(63) Continuation-in-part of application No. 15/840,283, filed on Dec. 13, 2017, now Pat. No. 11,512,305.

(60) Provisional application No. 62/434,507, filed on Dec. 15, 2016.

(51) Int. Cl.
*C12P 7/56* (2006.01)
*C12N 11/02* (2006.01)
*C12N 11/14* (2006.01)
*B82Y 15/00* (2011.01)
*B82Y 5/00* (2011.01)

(52) U.S. Cl.
CPC ............ *C12P 7/56* (2013.01); *C12N 11/02* (2013.01); *C12N 11/14* (2013.01); *B82Y 5/00* (2013.01); *B82Y 15/00* (2013.01); *C12Y 102/01012* (2013.01); *C12Y 102/02003* (2013.01); *C12Y 207/01002* (2013.01); *C12Y 207/01011* (2013.01); *C12Y 401/02013* (2013.01); *C12Y 503/01001* (2013.01); *C12Y 503/01009* (2013.01)

(58) Field of Classification Search
CPC ......... C12N 11/02; C12N 11/14; C12N 11/06; C12N 11/18; B82Y 15/00
See application file for complete search history.

(56) References Cited

U.S. PATENT DOCUMENTS

| | | | |
|---|---|---|---|
| 2014/0134700 A1* | 5/2014 | Lu | A61P 39/02 435/175 |
| 2016/0168559 A1* | 6/2016 | Shahgaldian | A61P 37/08 435/177 |

OTHER PUBLICATIONS

Kang W et al. Cascade Biocatalysis by Multienzyme-Nanoparticle Assemblies. 2014. Bioconjugate Chemistry. 25, 1387-1394. (Year: 2014).*

Beeckmans S et al. Clustering of Sequential Enzymes in the Glycolytic Pathway and the Citric Acid Cycle. 1990. Journal of Cellular Biochemistry. 43:297-306 (Year: 1990).*

Misset O et al. Glycolytic enzymes of Trypanosoma brucei. 1986. European Journal Biochemistry. 157, 441-453. (Year: 1986).*

Kang W et al. Electronic Supplementary Information for Cascade biocatalysis by multienzyme-nanoparticle assemblies. 2014. Bioconjugate Chemistry. p. 1-16.*

* cited by examiner

*Primary Examiner* — Paul J Holland
(74) *Attorney, Agent, or Firm* — US Naval Research Laboratory; Roy Roberts

(57) ABSTRACT

A nanoplatelet serves as a substrate for immobilizing enzymes involved in consecutive reactions as a cascade. This results in a significant increase in the rate of catalysis as well as final product yield compared to non-immobilized enzymes or enzymes immobilized to quantum dots.

6 Claims, 10 Drawing Sheets

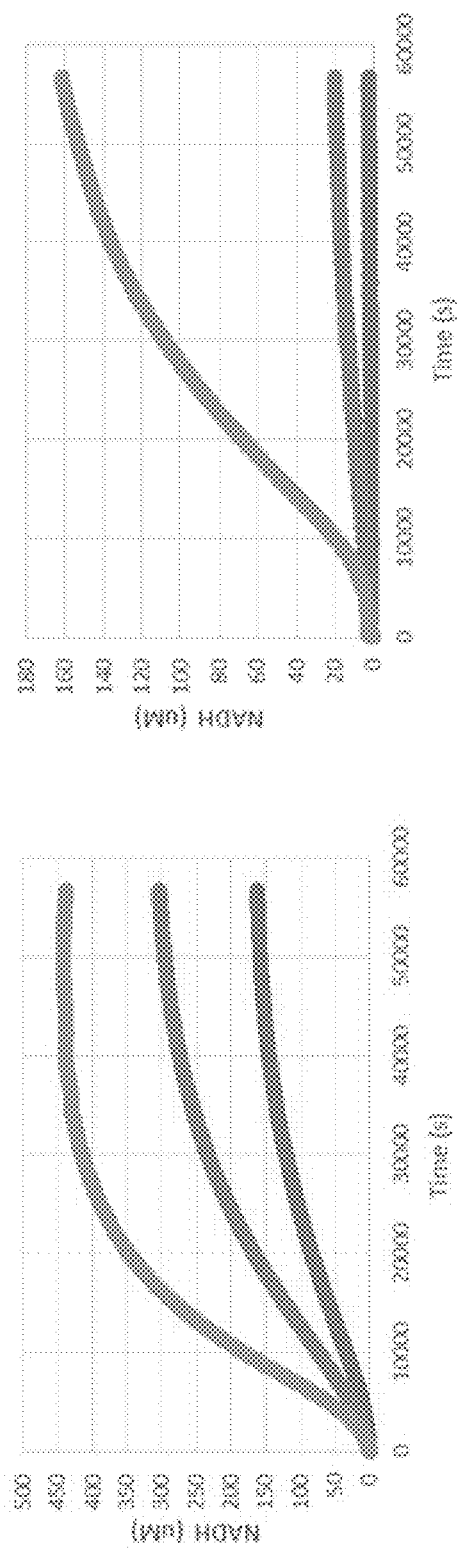
FIG. 7A
FIG. 7B
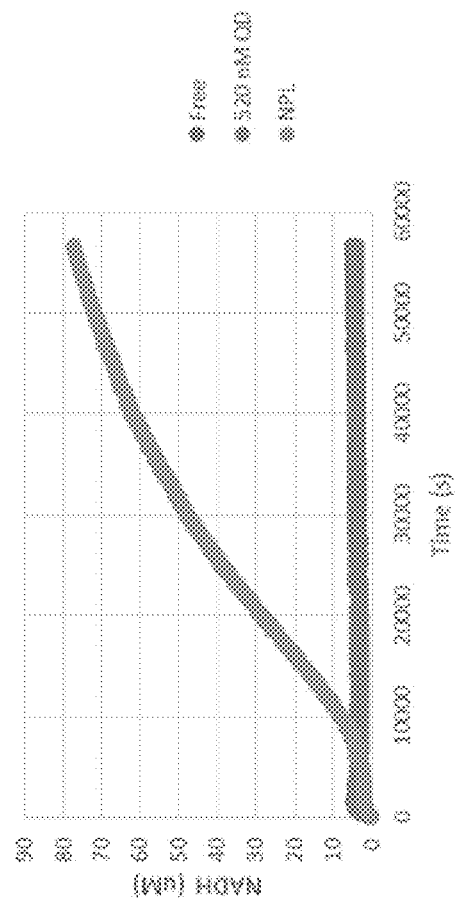
FIG. 7C

SELF-ASSEMBLED NANOPLATELET-ENZYME BIOCONJUGATES PROVIDING FOR INCREASED BIOCATALYTIC EFFICIENCY

CROSS-REFERENCE TO RELATED APPLICATIONS

This Application claims the benefit of U.S. Patent Application Nos. 62/434,507 filed on Dec. 15, 2016 and Ser. No. 15/840,283 filed on Dec. 13, 2017, the entirety of each of which is incorporated herein by reference.

BACKGROUND

Immobilized enzymes are of considerable interest for industrial and clinical purposes since immobilization allows for the reuse of enzymes, facile separation of enzymes and products, and often leads to enhanced physicochemical stability of the enzymes. However, immobilization of enzymes on large surfaces also leads to diminished activity of the bound enzyme. In contrast, immobilization of enzymes on nanoparticles (NPs) has been shown to often result in an increase in enzymatic activity. A need exists for further improvements in enzymatic activity.

BRIEF SUMMARY

In one embodiment, an enzymatic cascade cluster includes a plurality of nanoplatelets associated together as a cluster, wherein each nanoplatelet is bound to a plurality of enzymes configured as an enzymatic cascade wherein the product of a first enzyme is the substrate of a second enzyme and so forth; and wherein the enzymatic cascade comprises at least two different enzymes.

Also contemplated is an embodiment wherein the nanoplatelets in the cluster are closely associated with one another such that, on average, each nanoplatelet is separated from the nearest neighboring nanoplatelet by a distance of no more than about one nanoplatelet diameter.

In a further embodiment, a method of conducting a cascade reaction includes providing a cascade cluster comprising a plurality of nanoplatelets associated together as a cluster, wherein each nanoplatelet is bound to a plurality of enzymes configured as an enzymatic cascade wherein the product of a first enzyme is the substrate of a second enzyme and so forth, wherein the enzymatic cascade comprises at least two different enzymes, and wherein the nanoplatelets in the cluster are closely associated with one another such that, on average, each nanoplatelet is separated from the nearest neighboring nanoplatelet by a distance of no more than about one nanoplatelet diameter; contacting the cascade cluster with a substrate of the first enzyme; and allowing a reaction to proceed so that each of the plurality of enzymes acts in succession to produce an end product, wherein the reaction is performed while minimizing stirring or mixing.

In another embodiment a method of preparing an enzymatic cascade cluster, the method includes contacting a plurality of nanoplatelets with a plurality of enzymes configured as an enzymatic cascade wherein the product of a first enzyme is the substrate of a second enzyme and so forth, wherein the enzymatic cascade comprises at least two different enzymes; thereby forming an enzymatic cascade cluster wherein the nanoplatelets in the cluster are closely associated with one another such that, on average, each nanoplatelet is separated from the nearest neighboring nanoplatelet by a distance of no more than about one nanoplatelet diameter.

BRIEF DESCRIPTION OF THE DRAWINGS

FIGS. 7A-7C provide data showing improved catalytic efficiency over a range of nanoparticle concentrations for enzyme-NFL clusters compared to enzymes attached to QDs or free in solutions with the enzymes of FIG. 6.

DETAILED DESCRIPTION

Definitions

Figure 1:
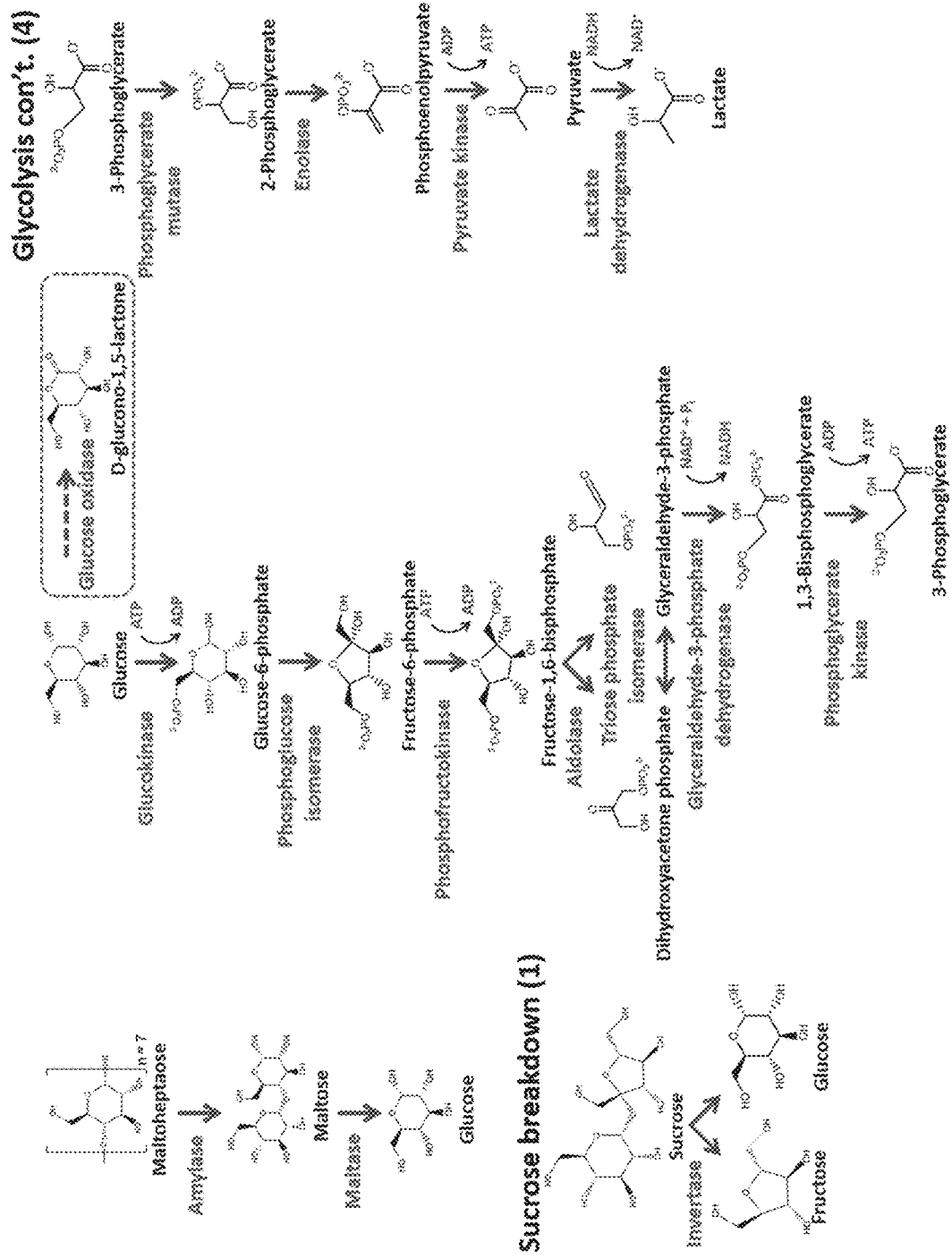
FIG. 1 illustrates thirteen of the enzymes associated with glycolysis.
Figure 2B:
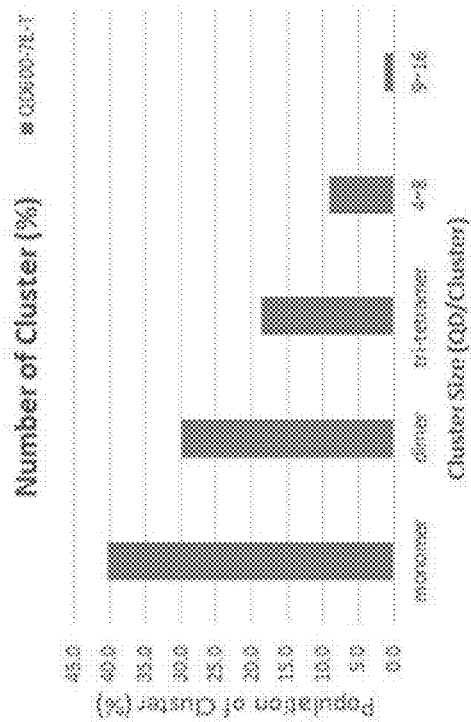
FIGS. 2A-2L show transmission electron microscope (TEM) analysis of enzyme-nanoparticle cluster formation.
Figure 2C:
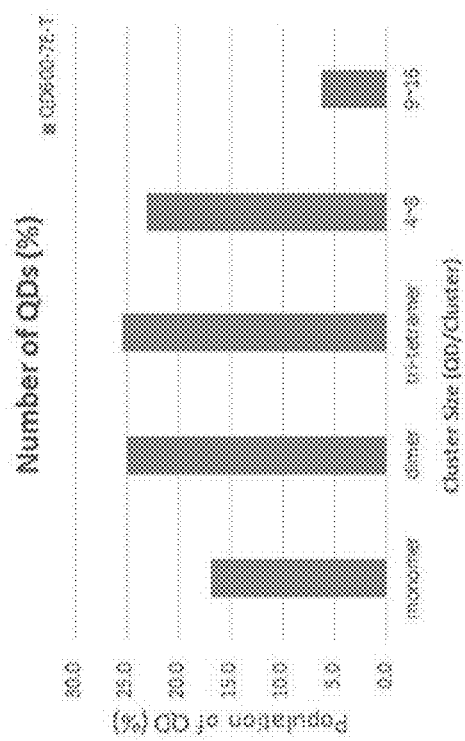
Figure 2A:
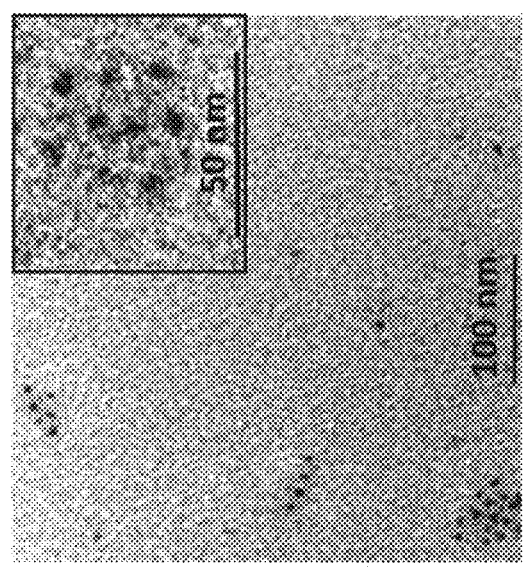
Figure 2E:
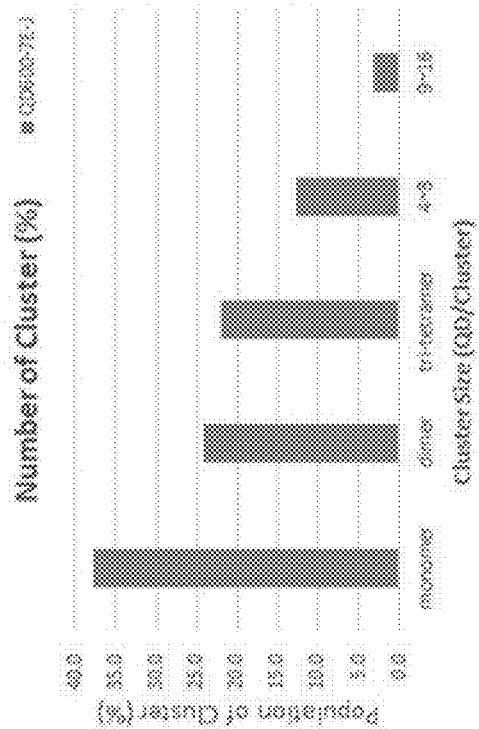
Figure 2F:
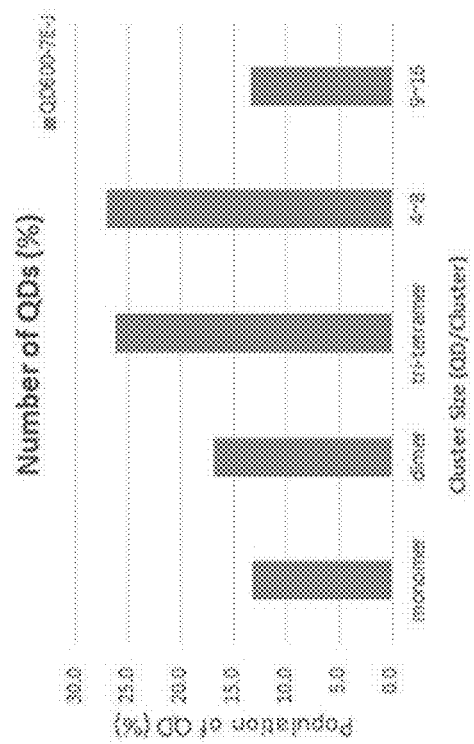
Figure 2D:
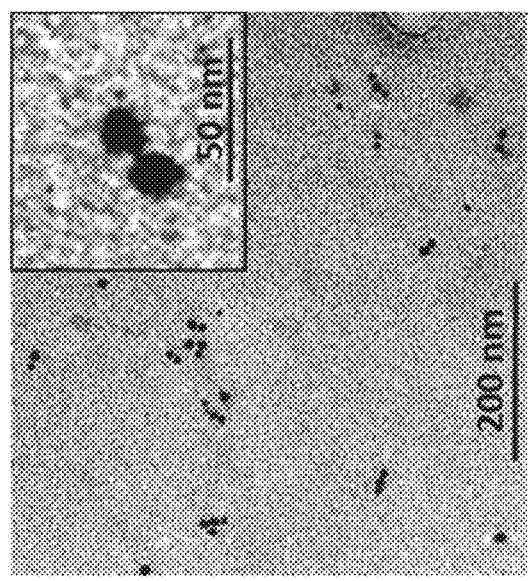
Figure 2H:
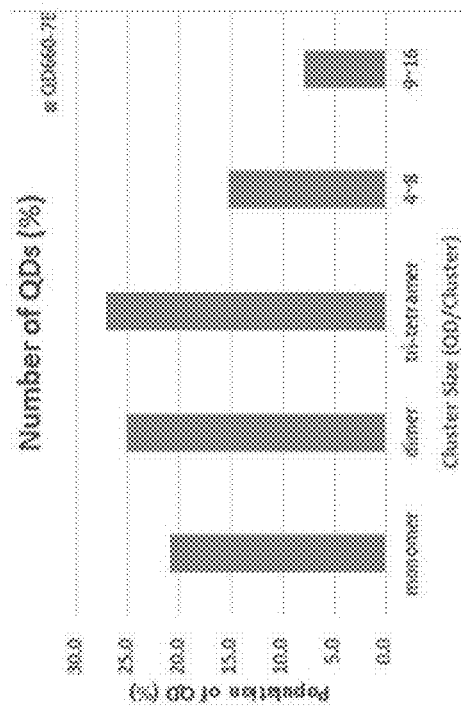
Figure 2I:
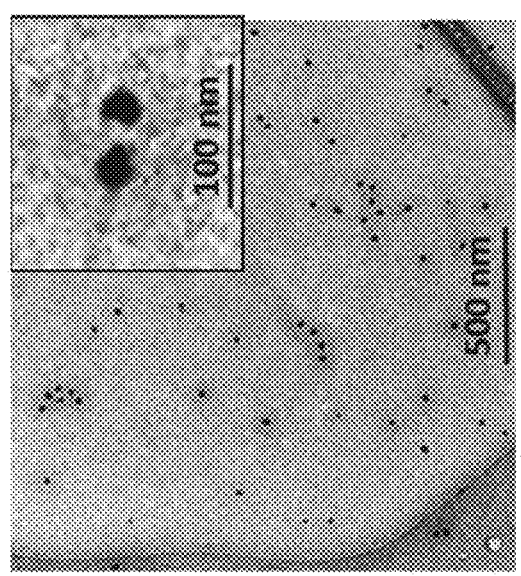
Figure 2G:
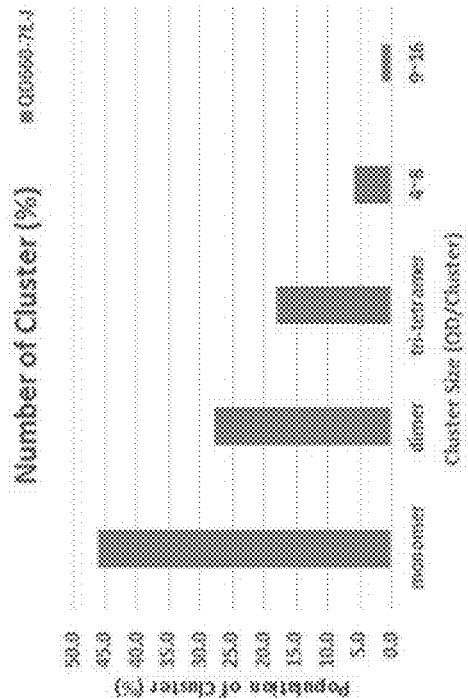
Figure 2K:
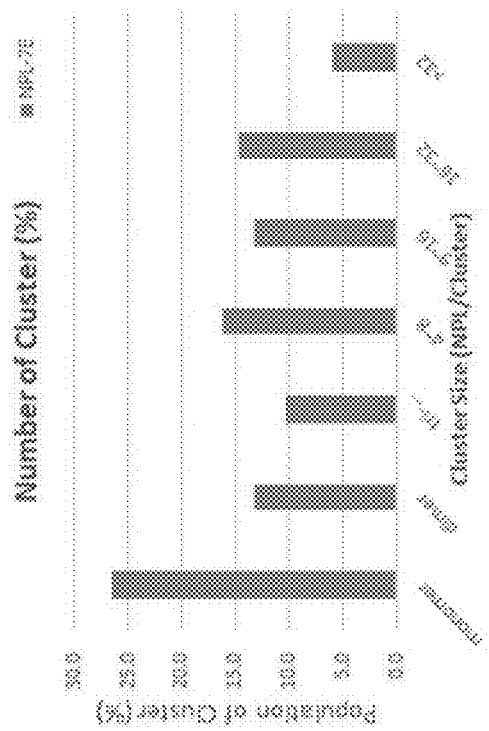
Figure 2L:
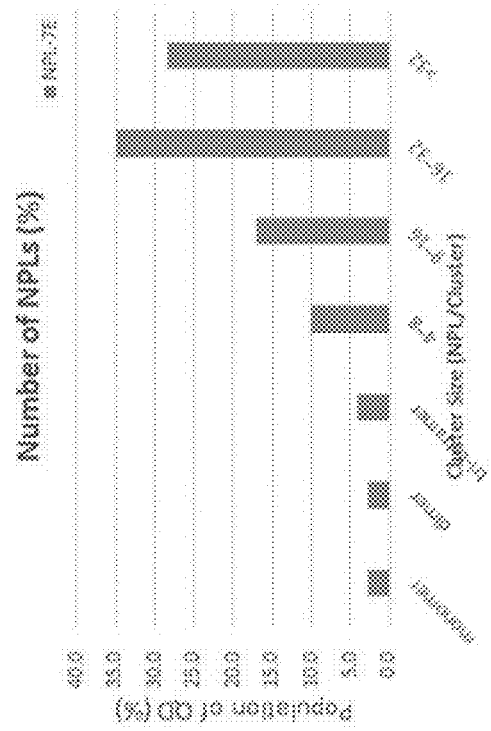
Figure 2J:
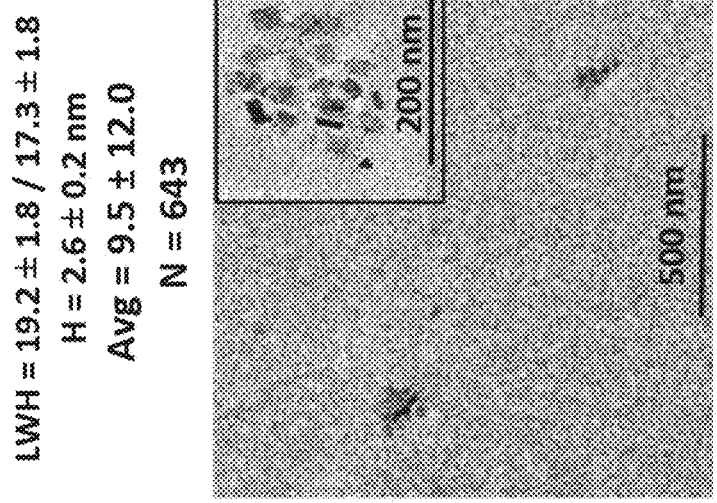

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below As used herein, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

The terms "semiconductor nanocrystal," "quantum dot," and "QD" are used interchangeably herein and refer to an inorganic crystallite of about 1 nm or more and about 1000 nm or less in diameter or any integer or fraction of an integer therebetween, preferably at least about 2 nm and about 50 nm or less in diameter or any integer or fraction of an integer therebetween, more preferably at least about 2 nm and about 20 nm or less in diameter (for example about 2, 3, 4, 5, 6, 7, 8, 9, 10, 11, 12, 13, 14, 15, 16, 17, 18, 19, or 20 nm). QDs are characterized by their relatively uniform nanometer size. A QD is capable of emitting electromagnetic radiation upon excitation (the QD is luminescent) and includes a "core" of one or more first semiconductor materials, with the core optionally surrounded by a "shell" of a second semiconductor material.

The term "nanoparticle" or "NP" as used herein includes the above-mentioned QDs in addition to other nano-scale and smaller particles such as metallic nanoparticles (e.g., nanoparticles comprising Ag, Au, Cu, Pd, Pt, and combinations thereof), carbon nanotubes, proteins, polymers, dendrimers, viruses, and drugs. A nanoparticle has a size of less than about 1 micron, optionally less than about 900, 800, 700, 600, 500, 400, 300, 200, 100, 80, 60, 50, 40, 30, 20, 10, 9, 8, 7, 6, 5, 4, 3, 2, or 1 nanometers. A nanoparticle may have various shapes such as a rod, a tube, a sphere, and the like. Nanoparticles may be made from various materials including metals, carbon (such as carbon nanotubes), polymers, and combinations thereof.

The term "nanoplatelet" or "NPL" refers to a nanoparticle with a non-spherical shape, including, for example, an oblate spheroid shape, or a quasi-two-dimensional and roughly circularly shape. In embodiments, NPLs have lateral dimensions from tens to hundreds of nanometers, and thicknesses of about 1 to 3 nm.

The term "nanomaterial" refers to a material having at least one dimension of less than 100 nm and that is not a naturally-occurring material. NPs and NPLs are normally considered nanomaterials.

Description

Industrial processes that involve many consecutive reactions can benefit from the use of enzymes, nature's catalysts. It has been shown that the stability of enzymes can be improved when immobilized on a surface allowing for reuse but sacrificing overall activity due to a number of factors. Also, co-localization of enzymes on a surface that are also part of a pathway have been shown to have an overall improved catalytic rate. It has been demonstrated that immobilizing one or two enzyme species to spherical nanoparticles can result in increased catalytic rate. It has also been shown that Zn-coated nanoparticles along with hexahistidine tagged enzymes can be self-assembled in a rapid, ratiometric, and facile manner.

As described herein, the use of nanoplatelets (NPLs) for the attachment of a number enzymes associated with a cascade reaction resulted in a vast improvement in activity compared to enzyme free in solution or enzymes attached to spherical nanoparticles. The increased catalytic efficiency and yield appears to result from to a combination of factors including enzyme stabilization, substrate channeling, and the ability of NPLs to interact with a greater number of enzyme species then spherical nanoparticles. Enzyme cascades attached to NPLs are resistant to parasitic enzymes free in solution confirming the presence of channeling and suggesting these constructs are resistant to fouling and off-site reactions.

Recently, advances in synthetic chemistry have provided control over the colloidal growth of CdSe quasi-2D (two-dimensional) NPL quantum wells. NPLs are atomically flat crystalline sheets, with lateral dimensions from tens to hundreds of nanometers, and tunable thicknesses with monolayer precision (e.g. 1-3 nm). Unlike spherical quantum dots (QDs) that confine excitons in three-dimensions, NPLs provide strong confinement in only one-dimension (thickness) with high uniformity. The 2D geometry imparts NPLs with many beneficial optical properties including sharp fluorescence spectra (~7 nm full width at half maximum), short fluorescence lifetimes, high quantum yields, and large molar absorption coefficients ($\sim 1\times 10^7$ $cm^{-1}M^{-1}$).

Standard laboratory techniques were used to perform these examples, for example as described in *Nanoscale*, 2017, 9, 5172-5187, incorporated herein by reference for the purposes of detailing methods for making and using the described nanoparticles.

Nanoplatelets cores of CdSe were prepared according to the methods described in S. Jana et al. *Langmuir*, 2015, 31 (38), 10532-10539. See also S. Ithurria and B. Dubertret, *J. Am. Chem. Soc.* 2008, 130, 16504-16505 and W. Cho, et al., *Chemistry of Materials* 2018 30 (20), 6957-6960. Each of these three documents is incorporated herein by reference for the purpose of disclosing methods of preparing and characterizing nanoplatelets.

In order to interface the NPLs with biological material, it can be helpful to have the NPLs soluble in water. When hydrophobic CdSe NPLs are transferred to water with conventional ligand exchange methods, the NPLs are unstable and lose their fluorescence. To overcome this problem, core CdSe NPLs were over-coated with ZnS to generate core/shell CdSe/ZnS NPLs. A ZnS shell was chosen to passivate the CdSe surface, minimize carrier delocalization, and to present a zinc-rich surface that is compatible with hydrophilic ligands and bioconjugation techniques based on polyhistidine coordination to the Zn on the NPL surface.

To add the ZnS shell to the CdSe core (CdSe/ZnS NPLs), the technique described in A. Polovitsyn et al. Chem. Mater 2017, 29(13), 5671-5680 was used. This document is incorporated herein by reference for the purpose of disclosing techniques for coating nanoparticles.

FIG. 1 illustrates thirteen of the enzymes associated with glycolysis which takes a linear polysaccharide (e.g. maltoheptaose) to lactate. Shown in the blue box is a possible side reaction by a parasitic enzyme which can divert substrate (glucose) in the middle of the reaction scheme and is used as part of a specific test for channeling. Invertase can be utilized to introduce more glucose into the system from sucrose.

Enzymes associated with glycolysis were assembled to NPLs through metal coordination chemistry between the rich zinc surface of the NPL and the oligohistidine tag associated with each enzyme. Multiple $(His)_6$ present in the enzymes contributed the formation of nanoclustered structures due to crosslinking Enzymes were allowed to assemble to NPLs for at least four hours. The order of enzyme addition to the NPLs does influence overall activity with the assembly in the forward direction of glycolysis yielding the best performance. As described in more detail below, enzymes attached to NPLs demonstrated higher activity and overall yield then when attached to QDs or free in solution. This enhancement was most noticeable at low nanoparticle concentrations where channeling phenomena are most apparent.

FIGS. 2A-2L show transmission electron microscope (TEM) analysis of enzyme-nanoparticle cluster formation. The seven enzymes associated with glycolysis from glucokinase to phophoglycerate kinase depicted in FIG. 1 were used, namely glucokinase, phosphoglucose isomerase, phosphofructokinase, aldolase, triose phosphate isomerase, glyceraldehyde-3-phosphate dehydrogenase, and phophoglycerate kinase. The enzymes were assembled to 520 nm (FIGS. 2A-2C), 600 nm (FIGS. 2D-2F), and 660 nm (FIGS. 2G-2I) QDs as well as nanoplatelets (NPLs) (FIGS. 2J-2L) with the enzymes all at the same concentration. Enzyme-NPL clusters containing the highest average number of nanoparticles per cluster as compared to QDs. Presumable, the NPL clusters also contained more enzymes per cluster then the other NP-cluster systems. These data also show that the materials form an emergent system with differing QDs or NPLs per cluster depending upon which is used.

Figure 3:
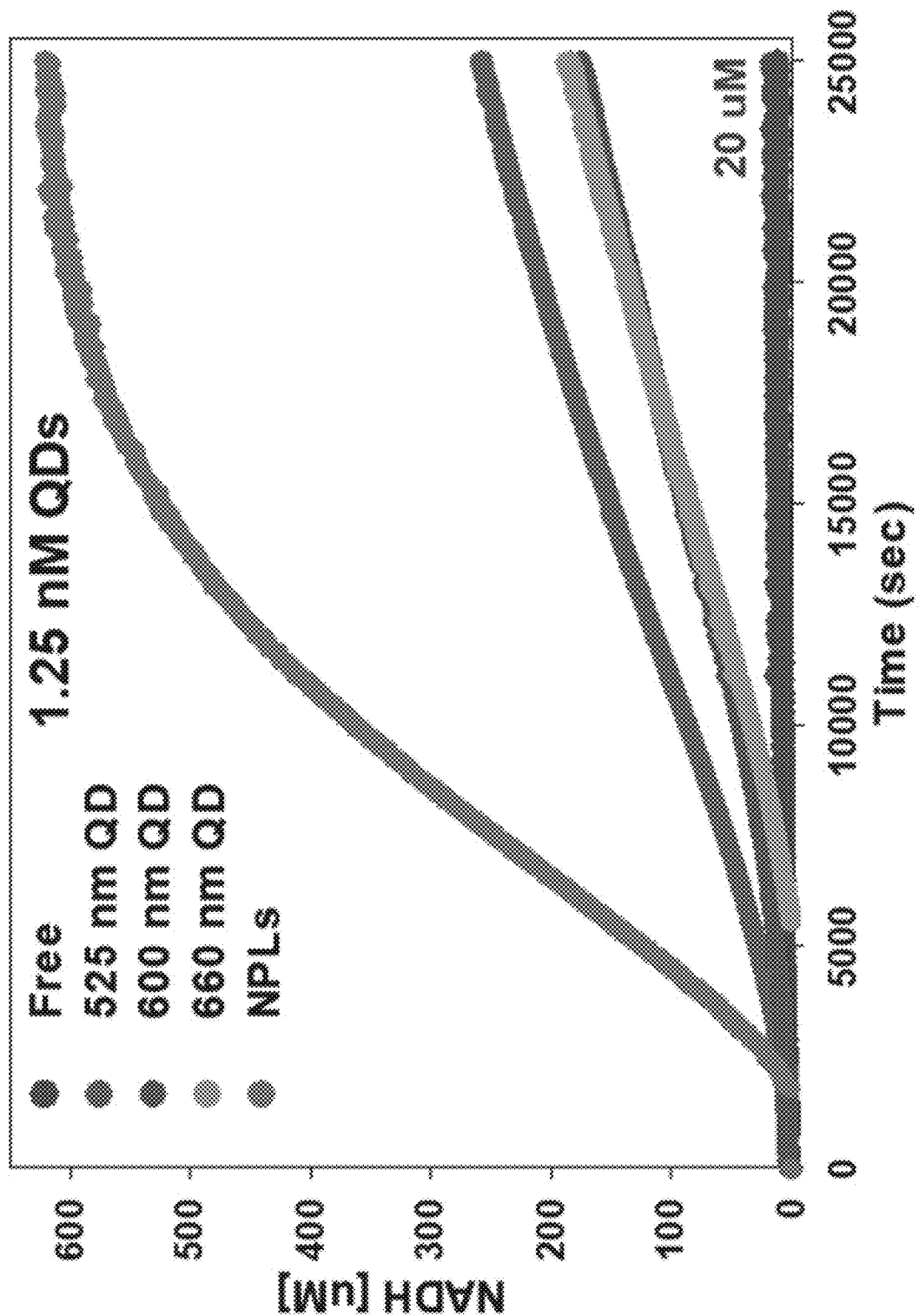
FIGS. 3 is a comparison in activity of seven enzymes attached to NPLs compared to different sized QDs and an equivalent amount of enzymes free in solution.

A comparison in activity of the seven enzymes attached to NPLs was made with different sized QDs and an equivalent amount of enzymes free in solution, with the results shown in FIG. 3. The nanoparticle concentration was kept constant at 1.25 nM while the enzyme concentration was a multiple of the nanoparticle concentration as a function of enzyme ratio. Enzyme-NPL clusters activity was more than double 525 nm QD activity while free enzyme solution was not significant. This shows that the NPL systems are far more efficient than the QDs or free enzymes, a surprising result.

Figure 4:
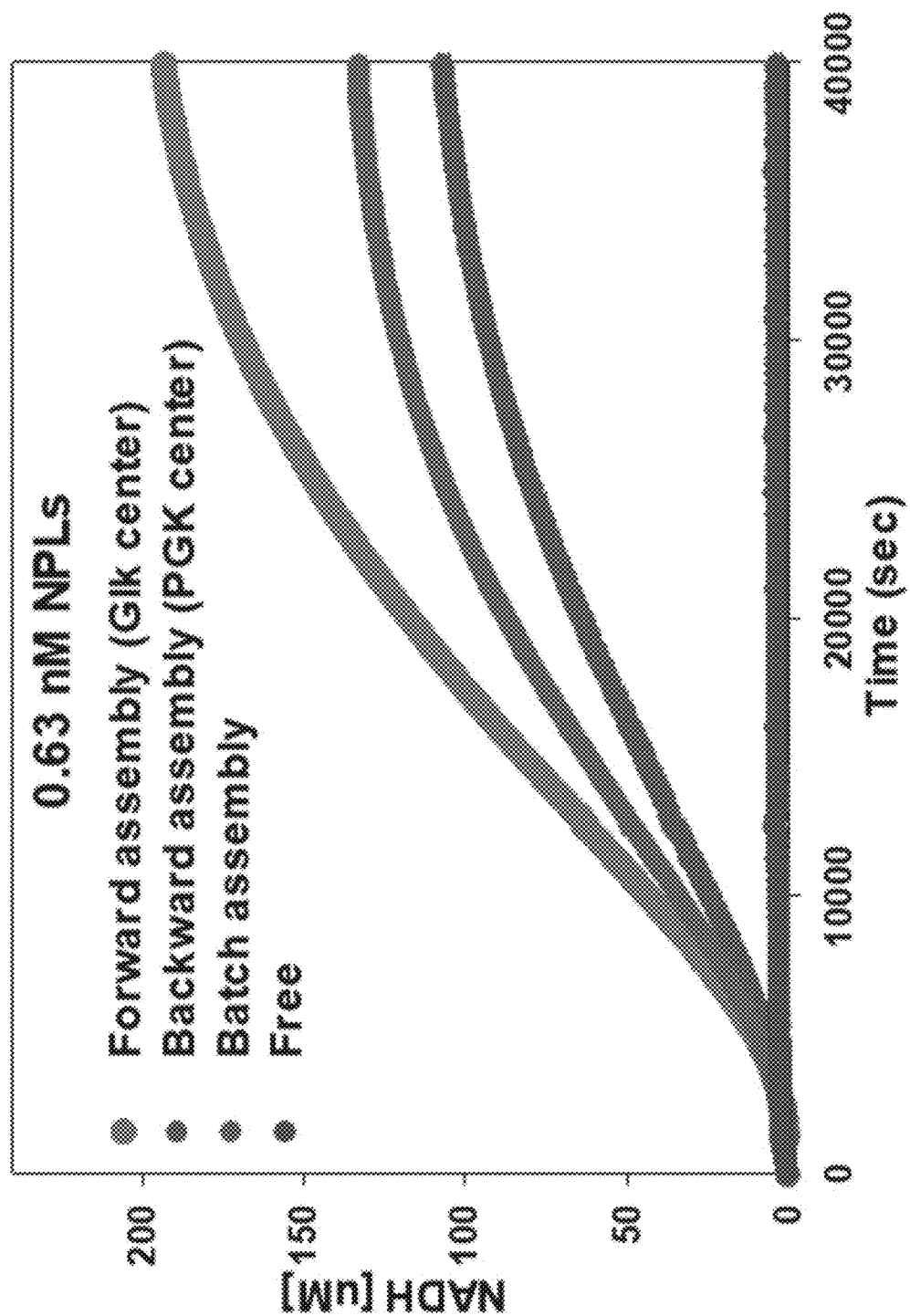
FIG. 4 illustrates how the order of enzyme assembly to NPLs influences the overall activity of the enzyme-NFL clusters.

The order of enzyme assembly to NPLs influences the overall activity of the enzyme-NPL clusters as seen in FIG. 4. The previously-mentioned seven enzymes from glucokinase to phophoglycerate kinase were investigated. The highest degree of activity is seen when Glk is added first to NPLs followed by each successive enzyme (sequential addition). However, assembling the enzymes randomly to the NPLs (batch) shows intermediate improvement in activity. Assembling the enzymes to the NPLs in a manner that reflects their sequential activity allows for better activity suggesting that some enzyme order or sequentiality is maintained.

Figure 5:
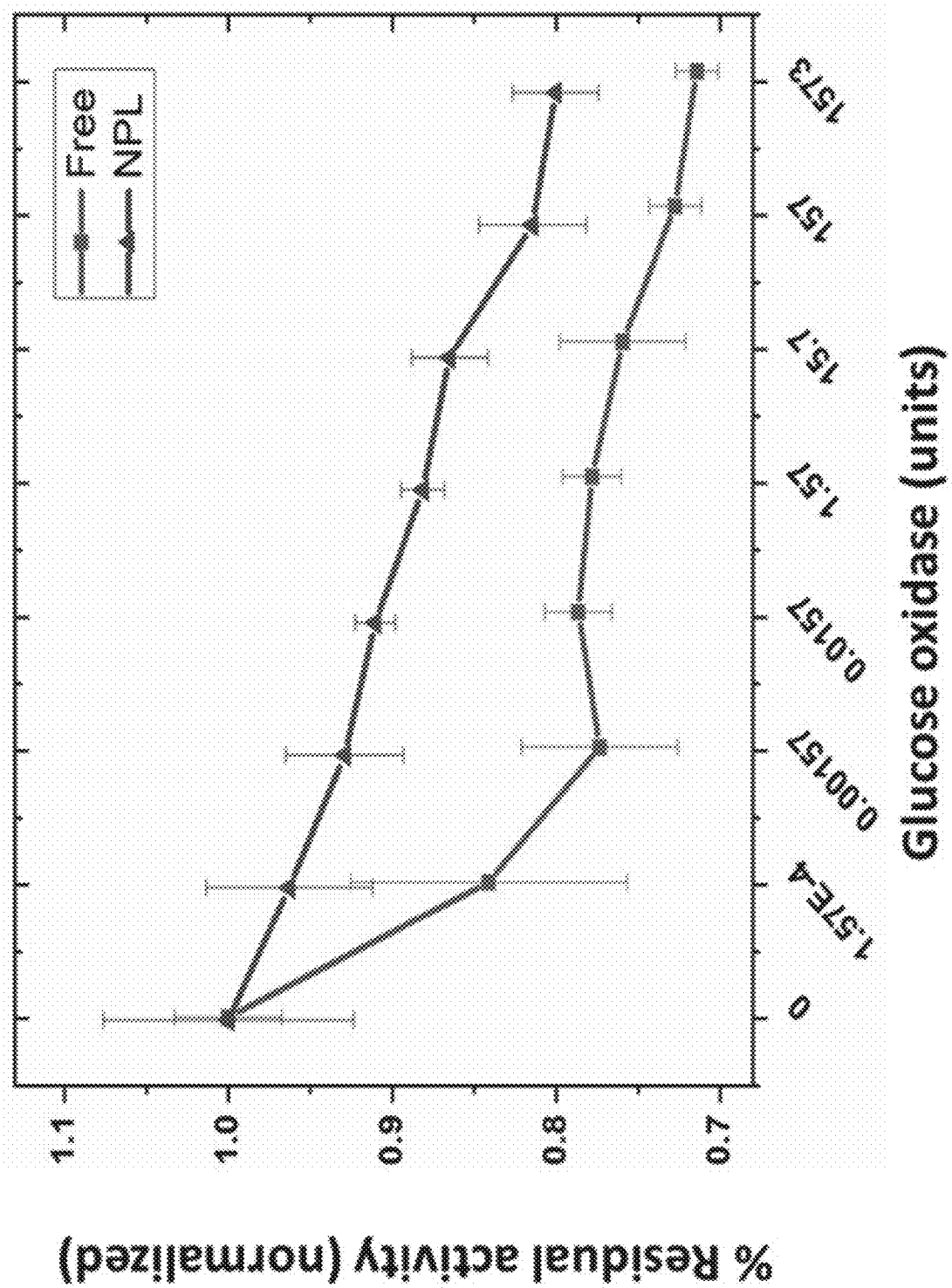
FIG. 5 shows data from nine enzymes from amylase to phophoglycerate kinase (in FIG. 1) attached to NPLs or free in solution in the presence of increasing amounts of a parasitic enzyme, glucose oxidase.

The nine enzymes associated with glycolysis (seen in FIG. 1) from amylase to phophoglycerate kinase (namely amylase, maltase, glucokinase, phosphoglucose isomerase, phosphofructokinase, aldolase, triose phosphate isomerase, glyceraldehyde-3-phosphate dehydrogenase, and phophoglycerate kinase) were attached to NPLs or free in solution in the presence of increasing amounts of a parasitic enzyme, glucose oxidase. Glucose oxidase removes glucose from the enzyme system therefore acting as parasitic or competitive enzyme. The key concept tested is whether the NPL-enzyme cluster would protect the glucose from being exposed and pulled away by the glucose oxidase. As shown in FIG. 5, enzyme-NPL clusters retain a higher degree of residual activity compared to free enzyme even at the highest amount glucose oxidase. This classical enzyme assay result confirms that substrate channeling is occurring within the enzyme-NFL cluster.

Figure 6:
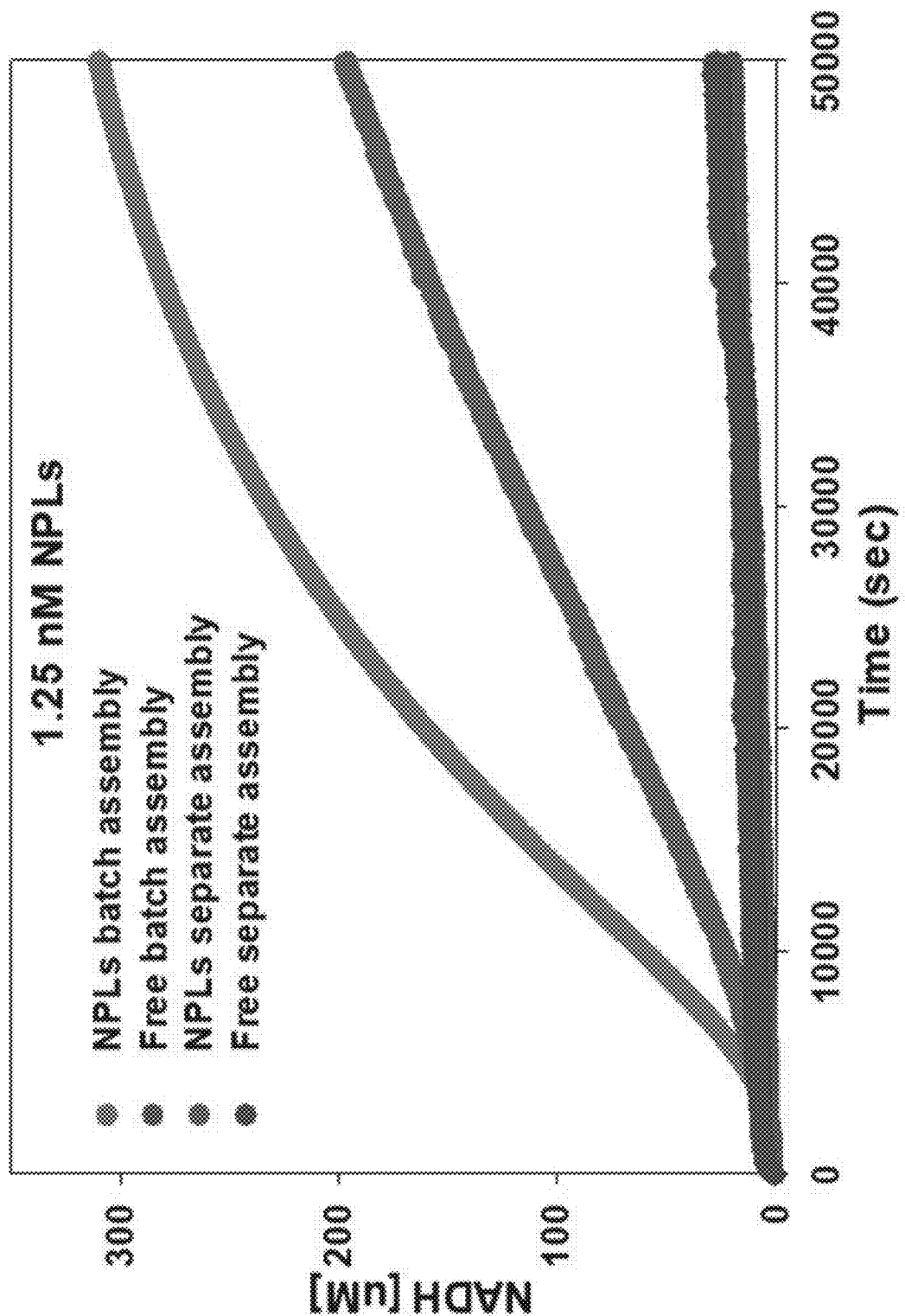
FIG. 6 has data showing how the method of cluster assembly is important for overall enzyme activity. The seven enzymes from glucokinase to phophoglycerate kinase (in FIG. 1) were either assembled each individually on NPLs and then combined together or were assembled all at once (batch) onto NPLs.

Cluster assembly is important for overall enzyme activity. The previously-described seven enzymes from glucokinase to phophoglycerate kinase were either assembled each individually on NPLs and then combined together or were assembled all at once (batch) onto NPLs. FIG. 6 presents data showing that batch assembling in a random manner provides increased activity compared to separate assembly, suggesting that individual NPLs added to solution containing different enzyme species and then forming clusters has better overall activity than individual NPLs containing discrete enzyme species added to solution and then forming clusters. This serves as further evidence that channeling behavior is occurring.

FIGS. 7A-7C provide data showing improved catalytic efficiency over a range of nanoparticle concentrations for enzyme-NFL clusters compared to enzymes attached to QDs or free in solutions. The assay uses seven enzymes from glucokinase to phophoglycerate kinase (in FIG. 1) associated with glycolysis. This suggest the NPLs are better able to stabilize enzymes when attached and that substrate channeling is occurring. The geometry of NPLs facilitates a greater number of enzymes to attach and form interconnecting clusters. Overall, the enzyme-NPL clusters demonstrate a higher rate of activity and efficiency especially as they are diluted.

SUMMARY

Synthetic biology promises to turn complex, heterogeneous chemical reactions with low yields into simple, green high-yield reaction systems. There are numerous industrial chemical reactions that already take advantage of enzymatic catalysis and enzyme immobilization methodologies but have limitations in enzyme stability and efficiency. Enzyme-NPL bioconjugates/clusters have the potential to be used in these systems achieving enzyme stability while improving efficiency, representing the potential for future use and sale. Due to NPL's unique geometry, a greater number of enzymes can be stabilized to the surface and a greater number of enzyme-NPL clusters can be formed compared to spherical nanoparticles. This "sandwiching" leads to greater enzymatic efficiency through enzyme stabilization and substrate channeling to a greater degree than seen in spherical nanoparticle systems. By utilizing enzymatic cascades with NPLs, an overall more durable catalyst with improved overall total turnover number is possible. This is a vast improvement over current immobilization technologies used in industrial processes which sacrifices enzyme efficiency for stability.

Alternatives

A person of ordinary skill in the art could attach enzymes using different techniques, not limited to $His_6$-Zn-QD or $His_6$-nitrilotriacetic acid (NTA)-NP. Examples of alternatives include the biotin-avidin system, cohesin-dockerin, SpyCatcher-SpyTag, and the like.

Advantages and Applications

Utilizing enzymes bound to metal-NPLs to enhance the performance of an enzymatic cascade offers the following advantages:

(1) Metal-NPLs can be easily functionalized with a wide variety of surface ligands that provide different surface charges, polarities, and steric bulk
(2) Enzymes can be easily and tightly bound to the surface through a simple hexahistidine tag, which can be incorporated genetically into the enzymes of interest
(3) The ability to site-specifically locate the hexahistidine tag on the enzyme allows for more uniform orientations of the enzymes on the surface
(4) NP attachment can often enhance the activity of individual bound enzymes
(5) Binding oligomeric enzymes to NPs via hexahistidine tags can stabilize the oligomeric structure at low concentrations and enhance activity
(6) The enhanced activity of a bound enzyme can be harnessed in an enzymatic cascade, either with a bound or unbound enzyme partner (for example, the enzyme partner can be unbound if tests determine that it operates more effectively unbound than bound).
(7) The co-localization of enzymes on a NP allows for substrate channeling, thus further enhancing the kinetics of the reaction
(8) Enzymes can be easily assembled on NPs in controlled ratios and controlled orientations
(9) One can easily adjust the ratios of enzymes bound to a NP to tune the pathway for different catalytic rates and pathway optimization
(10) One can assemble custom enzymatic pathways that do not exist in nature and may generate products that would be toxic to a host organism.
(11) The large surface area of NPs allows for the conjugation of numerous enzymes to the surface
(12) Enzymes can be stabilized by binding to a NP surface
(13) Substrates/intermediates appear to accumulate near NP surfaces which may further facilitate substrate channeling between multiple bound enzymes

(14) If assembled on a magnetic NP, the magnetic NP could be used to remove material and or sequentially add the NP-enzymes to control and alter the chemistry.

Numerous industrial chemical reactions take advantage of enzymatic biocatalysis and enzyme immobilization methodologies. This technique has the potential to be used in such reactions since, contrary to most immobilization strategies, it enhances enzymatic activity (rather than resulting in a loss of activity), stabilizes the bound enzymes, and increases the kinetic efficiency of cascade reactions via what appears to be similar to a substrate channeling mechanism. The result is a more durable catalyst with a much improved total turn-over number.

In embodiments, the technique is used to conduct a cascade of enzyme-catalyzed reactions in a completely cell-free environment, with the reaction product(s) easily separated from the nanoparticle-bound enzymes.

Furthermore, the technique could be used for the enzymatic detection of metabolites and small molecules in clinical and other types of samples, by allowing for increased longevity of the enzymes and enhanced signal production rates. Thus, a wide variety of enzymatic assays might be improved.

Enzymes are currently used commercially in industry and pharmaceutical synthesis to catalyze various transformations, thus a NP-enzyme construct could serve in this role. Embodiments might have two, three, four, five, six, seven, eight, nine, ten, or more enzymes configured as a cascade where the product of a first enzyme is the substrate of a second enzyme, and so on.

Concluding Remarks

All documents mentioned herein are hereby incorporated by reference for the purpose of disclosing and describing the particular materials and methodologies for which the document was cited.

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

REFERENCES

[1] Vranish, J. N., Ancona, M. G., Oh, E., Susumu, K., Medintz, I. L. (2017) *Nanoscale* 9, 5172-5187

[2] Vranish, J. N., Ancona, M. G., Walper, S. A., Medintz, I. L.(2018) Pursuing the Promise of Enzymatic Enhancement with Nanoparticle Assemblies, *Langmuir* 34, 2901-2925

[3] Ansari, S. A., and Husain, Q. (2012) Potential applications of enzymes immobilized on/in nano materials: A review, *Biotechnology Advances* 30, 512-523.

[4] Blanco-Canosa, J. B., Wu, M., Susumu, K., Petryayeva, E., Jennings, T. L., Dawson, P. E., Algar, W. R., and Medintz, I. L. (2014) Recent progress in the bioconjugation of quantum dots, *Coordin Chem Rev* 263, 101-137.

[5] Breger, J. C., Ancona, M. G., Walper, S. A., Oh, E., Susumu, K., Stewart, M. H., Deschamps, J. R., and Medintz, I. L. (2015) Understanding How Nanoparticle Attachment Enhances Phosphotriesterase Kinetic Efficiency, *ACS Nano* 9, 8491-8503.

[6] Breger, J. C., Walper, S. A., Oh, E., Susumu, K., Stewart, M. H., Deschamps, J. R., and Medintz, I. L. (2015) Quantum dot display enhances activity of a phosphotriesterase trimer, *Chem Commun* 51, 6403-6406.

[7] Brown, C. W, Oh, E., Hastman, D. A., Walper, S. A., Susumu, K., Stewart, M. H., Deschamps, J. R., and Medintz, I. L. (2015) Kinetic enhancement of the diffusion-limited enzyme beta-galactosidase when displayed with quantum dots, *RSC Adv* 5, 93089-93094.

[8] Claussen, J. C., Malanoski, A., Breger, J. C., Oh, E., Walper, S. A., Susumu, K., Goswami, R., Deschamps, J. R., and Medintz, I. L. (2015) Probing the Enzymatic Activity of Alkaline Phosphatase within Quantum Dot Bioconjugates, *J Phys Chem C* 119, 2208-2221.

[9] Es, I., Vieira, J. D. G., and Amaral, A. C. (2015) Principles, techniques, and applications of biocatalyst immobilization for industrial application, *Appl Microbiol Biot* 99, 2065-2082.

[10] Fu, J. L., Liu, M. H., Liu, Y., Woodbury, N. W, and Yan, H. (2012) Interenzyme Substrate Diffusion for an Enzyme Cascade Organized on Spatially Addressable DNA Nanostructures, *J Am Chem Soc* 134, 5516-5519.

[11] Johnson, B. J., Algar, W. R., Malanoski, A. P., Ancona, M. G., and Medintz, I. L. (2014) Understanding enzymatic acceleration at nanoparticle interfaces: Approaches and challenges, *Nano Today* 9, 102-131.

[12] Sapsford, K. E., Pons, T., Medintz, I. L., Higashiya, S., Brunel, F. M., Dawson, P. E., and Mattoussi, H. (2007) Kinetics of metal-affinity driven self-assembly between proteins or peptides and CdSe-ZnS quantum dots, *J Phys Chem C* 111, 11528-11538.

[13] S. Jana et al. *Langmuir,* 2015, 31 (38), 10532-10539.

[14] S. Ithurria and B. Dubertret, *J. Am. Chem. Soc.* 2008, 130, 16504-16505.

[15] W. Cho, et al., *Chemistry of Materials* 2018 30 (20), 6957-6960.

What is claimed is:

1. A method of conducting a cascade reaction, comprising:
   providing a cascade cluster comprising a plurality of nanoplatelets associated together as a cluster, wherein each nanoplatelet is bound to a plurality of enzymes configured as an enzymatic cascade wherein the product of a first enzyme is the substrate of a second enzyme and so forth, wherein the enzymatic cascade comprises at least two different enzymes, and wherein the nanoplatelets in the cluster are closely associated with one another such that, on average, each nanoplatelet is separated from the nearest neighboring nanoplatelet by a distance of no more than about one nanoplatelet diameter;
   contacting the cascade cluster with a substrate of the first enzyme; and
   allowing a reaction to proceed so that each of the plurality of enzymes acts in succession to produce an end product,
   wherein the reaction is performed without stirring or mixing.

2. The method of claim 1, wherein the nanoplatelet comprises zinc and the enzymes are bound to the nanoplatelet via polyhistidine sequences in the enzymes.

3. The method of claim 1, wherein said plurality of enzymes comprises glucokinase, phosphoglucose isomerase, phosphofructokinase, aldolase, triose phosphate isomerase, glyceraldehyde-3-phosphate dehydrogenase, and phophoglycerate kinase.

4. A method of preparing an enzymatic cascade cluster, the method comprising:

contacting a plurality of nanoplatelets with a plurality of enzymes configured as an enzymatic cascade wherein the product of a first enzyme is the substrate of a second enzyme and so forth, wherein the enzymatic cascade comprises at least two different enzymes; thereby forming an enzymatic cascade cluster wherein the nanoplatelets in the cluster are closely associated with one another such that, on average, each nanoplatelet is separated from the nearest neighboring nanoplatelet by a distance of no more than about one nanoplatelet diameter, wherein at least one of the enzymes comprises multiple $(His)_6$ tags effective to cross-link the nanoplatelets into the cluster.

5. The method of claim 4, wherein the contacting is made in a batch fashion with the entire plurality of enzymes mixed with the nanoplatelets essentially simultaneously.

6. The method of claim 4, wherein the contacting is made sequentially.

\* \* \* \* \*